US00PP34397P2

(12) United States Plant Patent
Rippetoe

(10) Patent No.: US PP34,397 P2
(45) Date of Patent: Jul. 5, 2022

(54) SHRUB ROSE PLANT NAMED 'RIPFIRST'

(50) Latin Name: *Rosa hybrida*
Varietal Denomination: 'RIPfirst'

(71) Applicant: Robert Neil Rippetoe, Rancho Mirage, CA (US)

(72) Inventor: Robert Neil Rippetoe, Rancho Mirage, CA (US)

( * ) Notice: Subject to any disclaimer, the term of this patent is extended or adjusted under 35 U.S.C. 154(b) by 0 days.

(21) Appl. No.: 17/327,698

(22) Filed: May 22, 2021

(51) Int. Cl.
*A01H 5/02* (2018.01)
*A01H 6/74* (2018.01)

(52) U.S. Cl.
USPC ..... Plt./106

(58) Field of Classification Search
USPC ..... Plt./101, 102, 106
See application file for complete search history.

(56) References Cited

PUBLICATIONS

Certified Roses: A work of Art 2022 catalog, http://www.certifiedrose.com/images/catalog.pdf. 3 pages. (Year: 2022).*
Facebook: Geetha's Garden post. May 2, 2019. https://www.facebook.com/510182212840912/posts/coral-miracle-shrub-rose/563796837479449/. 7 pages. (Year: 2019).*

* cited by examiner

*Primary Examiner* — Karen M Redden

(57) ABSTRACT

A new and distinct cultivar of shrub rose having a compact and rounded growth habit, for landscape use named 'RIPfirst' is disclosed, characterized by double, coral pink petals and continuous flowering.

5 Drawing Sheets

Botanical/commercial classification:
Latin name—*Rosa hybrida.*
Common name—Shrub Rose Plant.
Varietal denomination: 'RIPfirst'.

BACKGROUND

'RIPfirst' is a new and distinct variety of shrub rose. 'RIPfirst' originated from a controlled hybridization in February 2011 in Rancho Mirage, Calif. between the female parent, 'Prairie Sunrise' variety (unpatented), and the male parent, an un-named and unpatented light pink shrub rose seedling.

The resulting seeds from the hybridization were planted and evaluated. 'RIPfirst' was selected October 2012 in Rancho Mirage, Calif. 'RIPfirst' was first asexually propagated in March 2013 in Litchfield Park, Ariz. by budding and grafting on the plant/rootstock of *Rosa hybrida* 'Dr. Huey' (unpatented) and subsequently by own root cuttings.

Other subsequent asexual propagations were conducted in controlled environments in Litchfield Park, Ariz. and Tyler, Tex. and demonstrate that 'RIPfirst' reproduces true to type in successive generations of asexual reproduction via softwood cuttings, budding, and grafting.

COMPARISON WITH PARENTAL AND COMMERCIAL LINES

'RIPfirst' may be distinguished from the female parent, 'Prairie Sunrise' cultivar (unpatented) by the following combination of characteristics: 'Prairie Sunrise' has apricot flowers, while 'RIPfirst' has coral flowers. 'Prairie Sunrise' has a semi-erect habit, while 'RIPfirst' has a compact habit. 'Prairie Sunrise' has 40 to 50 petals, while 'RIPfirst' has 20 to 25 petals.

'RIPfirst' may be distinguished from the male parent, an un-named shrub rose plant by the following combination of characteristics: the male parent has light pink flowers, while 'RIPfirst' has coral flowers. The male parent has an upright habit, while 'RIPfirst' has a compact habit. The male parent also has 30 to 35 petals, while 'RIPfirst' has 20 to 25 petals.

'RIPfirst' may be distinguished from its closest commercially available cultivar, 'RADral' (U.S. Plant Pat. No. 19,803) by the following combination of characteristics: 'RADral' has a loose plant habit compared to the compact habit of 'RIPfirst'. 'RADral' has a bloom color that lightens with age, while 'RIPfirst' has a bloom color that slightly darkens with age. 'RIPfirst' is also considerably smaller than 'RADral' plant (80 cm tall versus 165 cm tall).

SUMMARY

The following are the most outstanding and distinguishing characteristics of this new cultivar when grown under normal horticultural practices in Litchfield Park, Ariz. and Tyler, Tex. 1. A shrub rose having a compact and mounding growth habit, suitable for landscape decoration; 2. Coral colored flowers borne continuously; and 3. Dense, medium green foliage.

DESCRIPTION OF THE DRAWING

This rose plant is illustrated by the accompanying illustrations that show as true as is reasonably possible to obtain in color photographs of this type, the typical characteristics of the buds, flowers, leaves, and stems, of 'RIPfirst'. The illustration was taken using conventional techniques and is as accurate as possible by conventional photographic techniques. The contrast shown is as true as can be reasonably obtained by conventional photographic procedures. The illustration is part of a 3- to 4-year-old rose plant grown outdoors in Tyler, Tex. in August 2020.

Specifically illustrated in FIG. 1 of the drawings are flower stages, viewed from above. The top left stage is the bud upon opening and sepals detached. The top right stage is approximately a day more mature, with petals maturing. The bottom left is further mature, with maximum petal expanditure before the petals begin to drop from the plant. The bottom right is the flower petals detached revealing reproductive flower parts.

Figure 1:
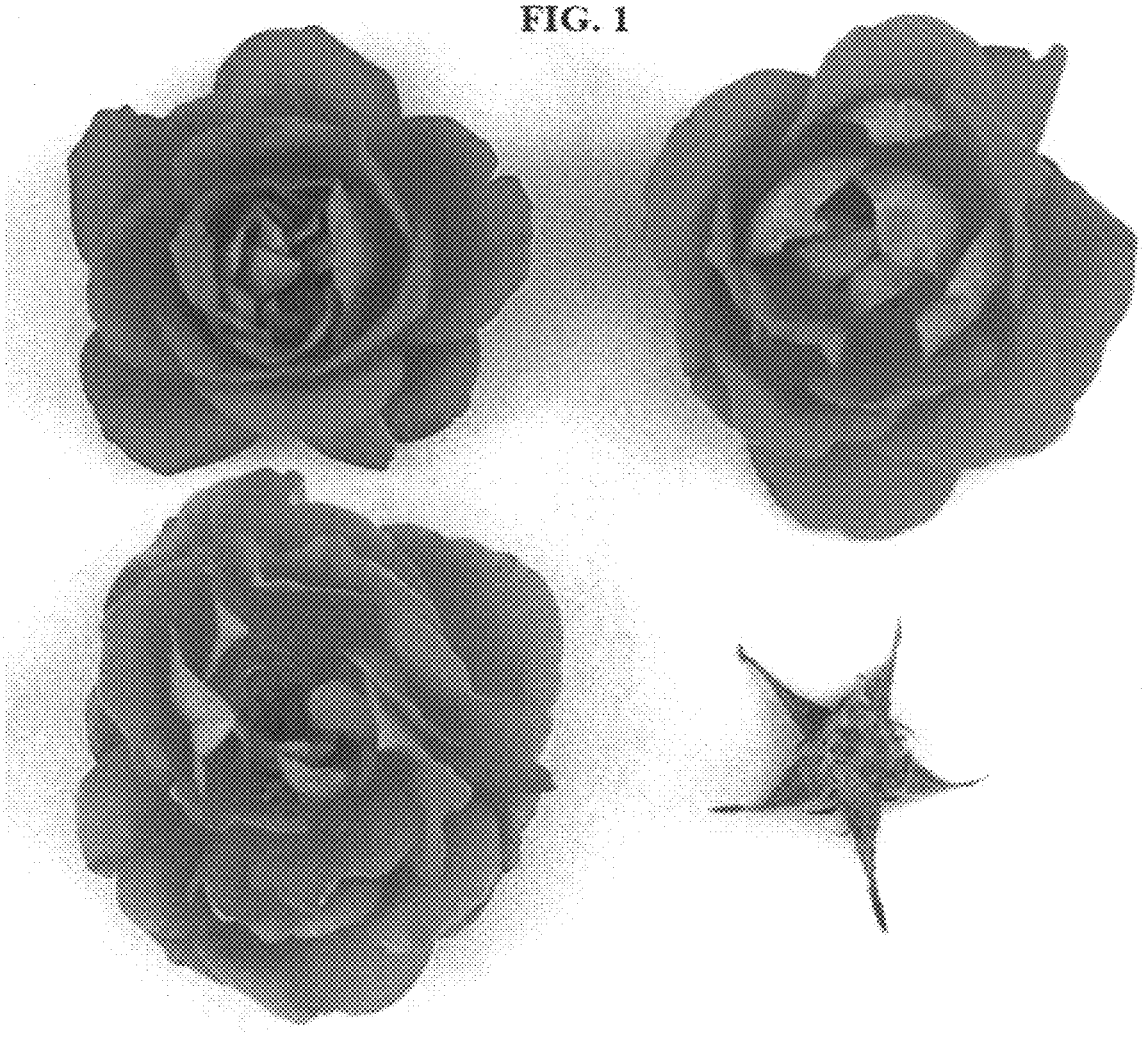
Figure 2:
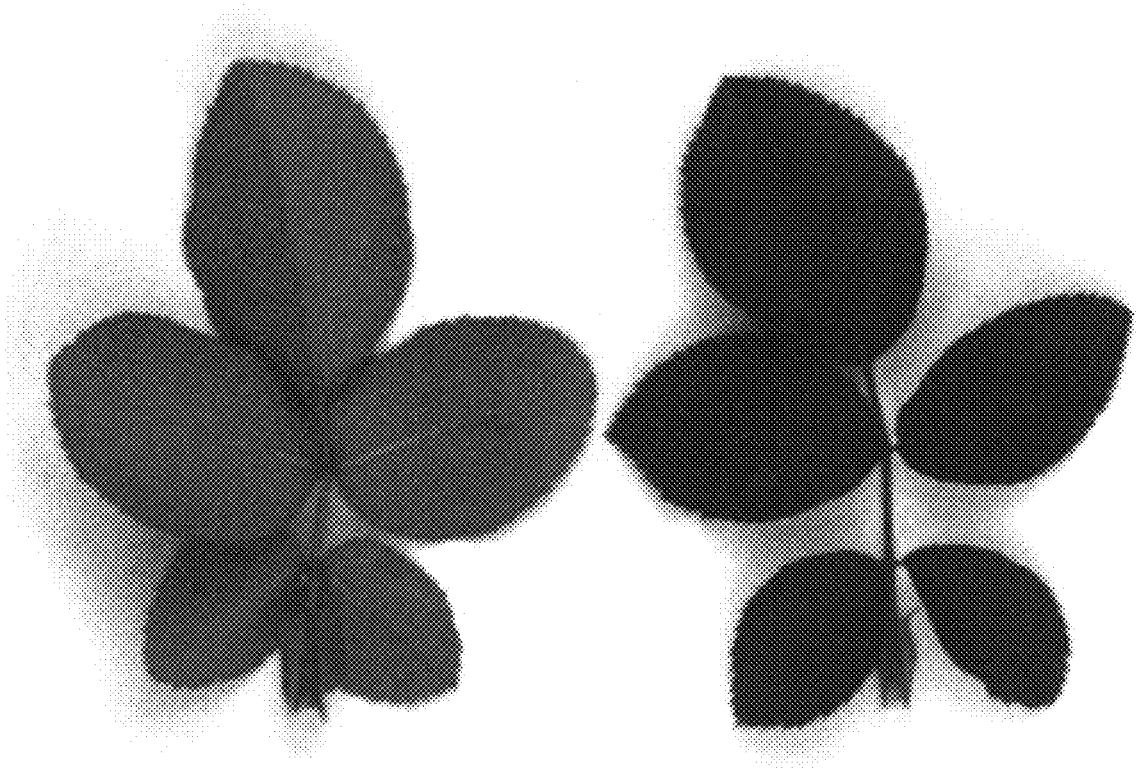

Specifically illustrated in FIG. 2 of the drawings are two leaves of 'RIPfirst'. The left leaf depicts the underside of the foliage in texture and color, and the right leaf depicts the top of the foliage in texture and color.

Figure 3:
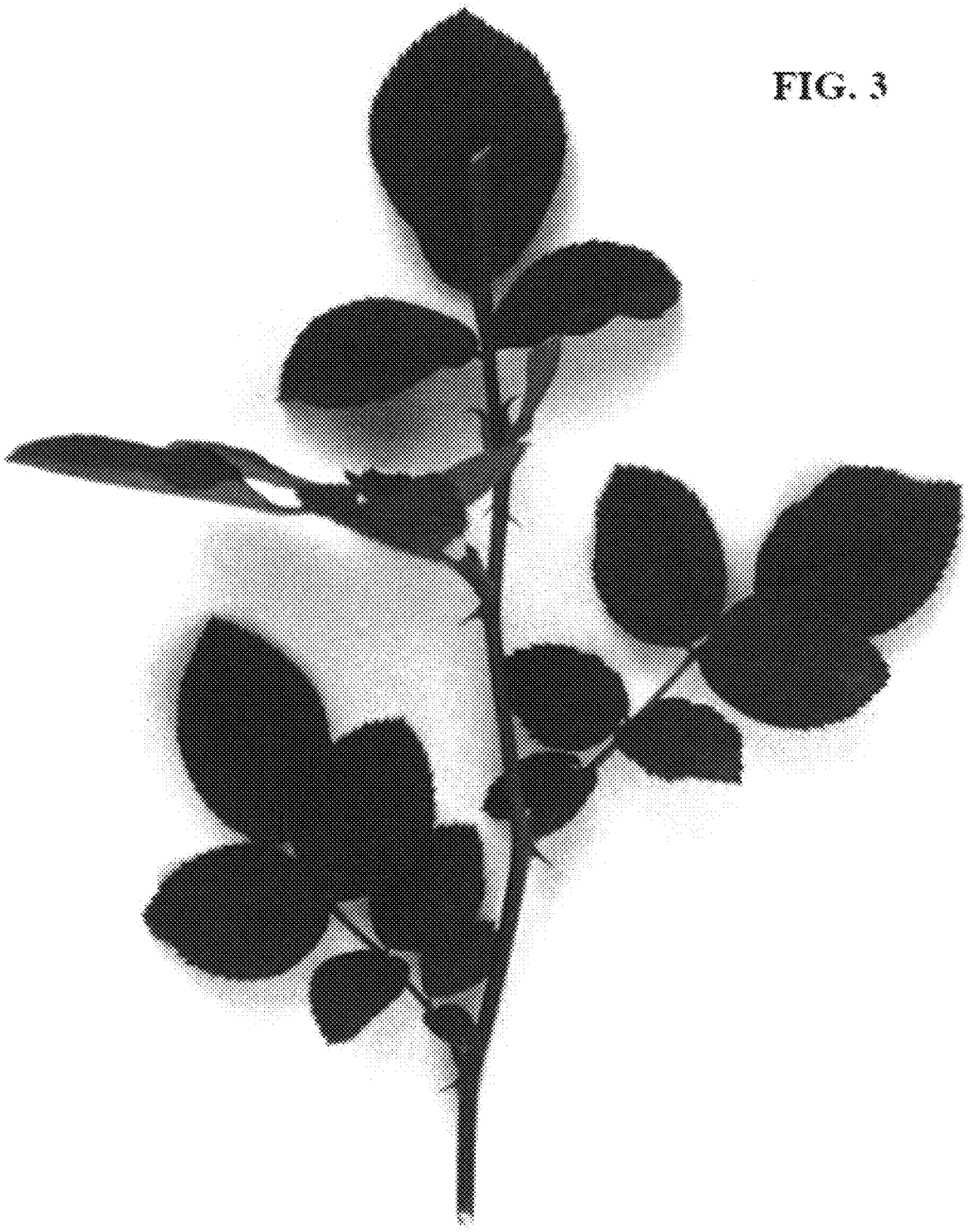

Specifically illustrated in FIG. 3 of the drawings is a mature stem with foliage, exhibiting prickles and stem color.

Figure 4:
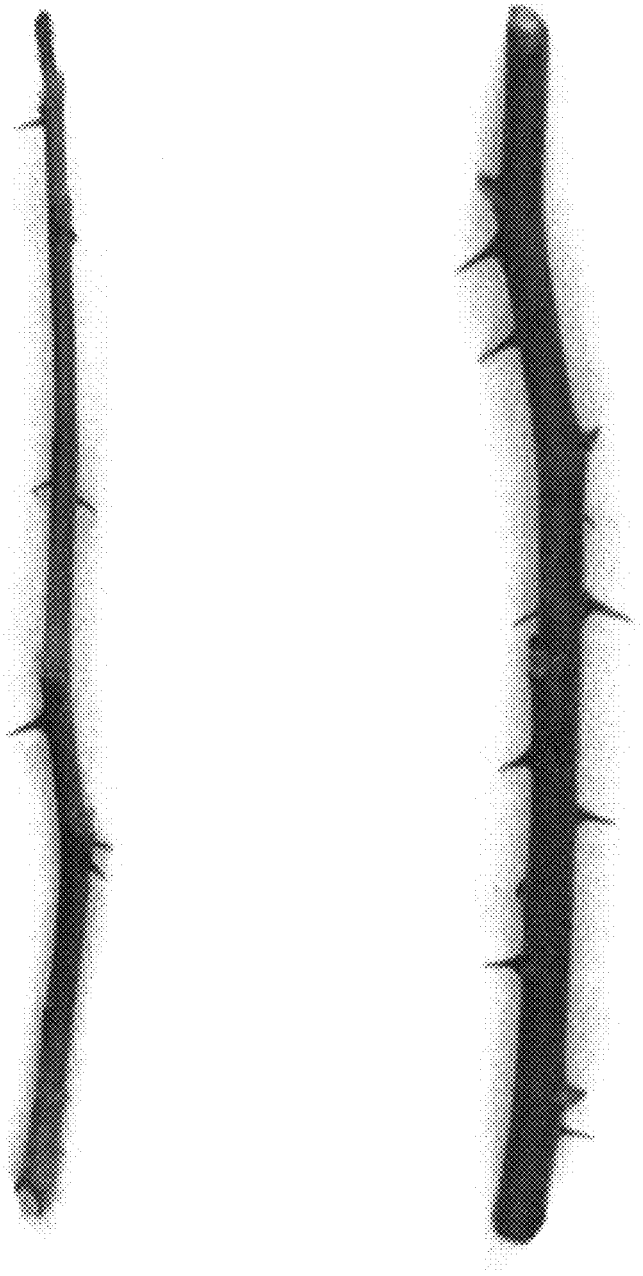

Specifically illustrated in FIG. 4 of the drawings are mature and juvenile stems, that are bare stem exhibiting prickles and stem color.

Figure 5:
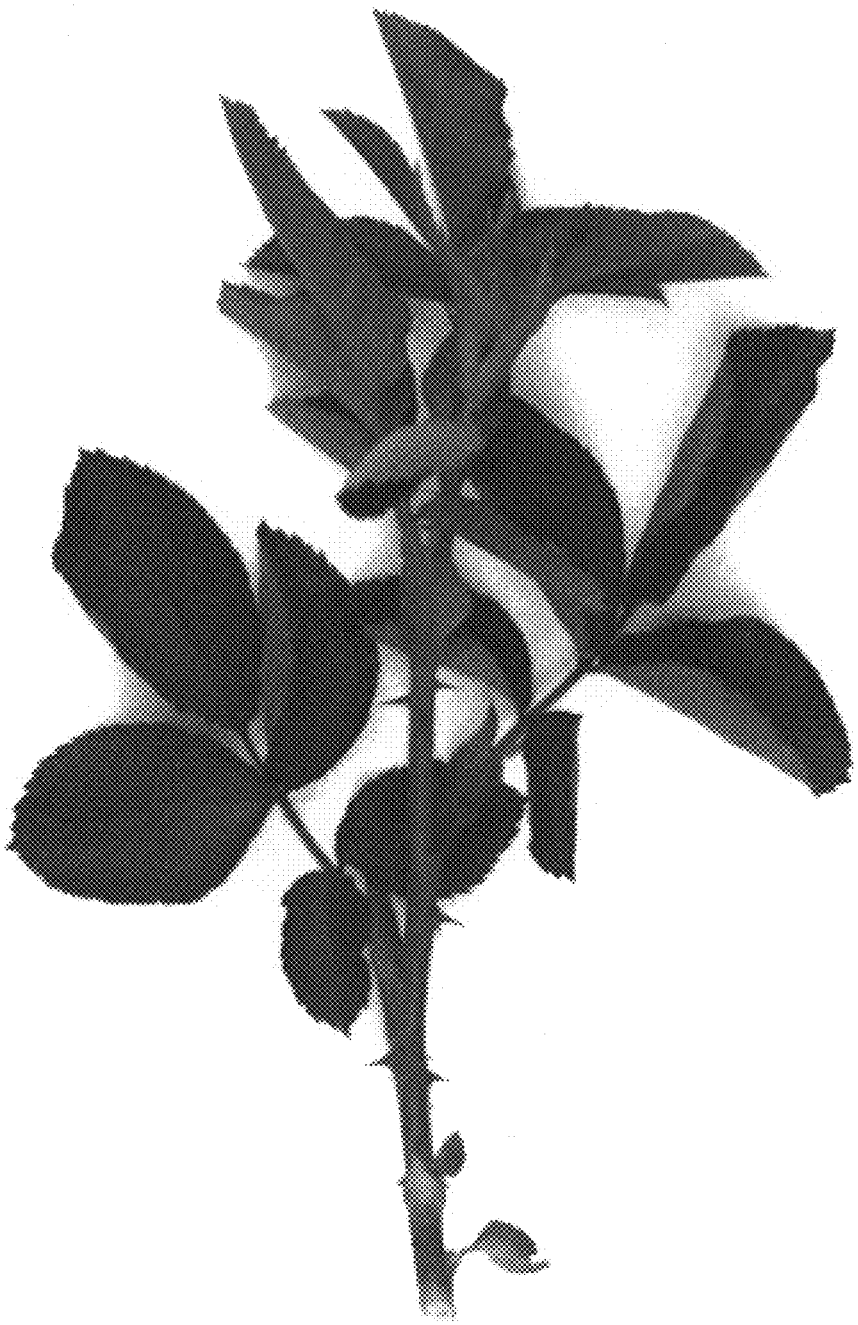

Specifically illustrated in FIG. 5 of the drawings is a juvenile shoot, with juvenile foliage, juvenile prickles, and a juvenile flower bud.

DETAILED DESCRIPTION

The chart used in the identification of the colors is that of The Royal Horticultural Society (R.H.S. Colour Chart, 2015 edition), London, England. The terminology which precedes reference to the chart has been added to indicate the corresponding color in more common terms. The description is based on the observation of 3 to 4-year old specimens of the new cultivar during August, while growing in an ornamental landscape on their own roots at Tyler, Tex., U.S.A.

Growth

The shrub rose plant has a compact and round growing habit, with an average height of 80 cm. and an average width of 90 cm. It displays very vigorous growth.

The color of the young stem is Yellow-Green Group N144C. The young stem bears prickles that average 5.5 mm. in length. The young stem prickles are almost straight to angled slightly downward with a small oval base; prickle color is Grayed-Orange Group 185D. The young stem bears an average of 8 prickles per 4" of stem. The color of the mature stem is Yellow-Green Group N148A. The mature stem bears prickles that average 6.5 mm. in length. The mature stem prickles are almost straight to angled slightly downward with a small oval base; prickle color is Greyed-Orange Group 177D. The mature stem bears an average of 14 prickles per 4" of stem.

The compound leaves are usually comprised of 5 to 7 leaflets and are borne abundantly. The mature five-leaflet leaves are about 8.5 cm. in length and about 9.5 cm. in width at the widest point, slightly rugose and smooth on both sides, and semi-glossy in finish on the upper side and matte in finish on the under side. The mature leaves have a pinnate venation pattern. Mature terminal leaflets average 6.1 cm. in length and 2.9 cm. in width at the widest point, shaped ovate. Their margins are usually serrulate.

The upper surface color of the mature leaf is Green Group 137A. The under-surface color of the mature leaf is Green Group 138B. The under and upper colors of the leaf veins on the mature leaf are similar in coloration to the upper and under surfaces colors of the mature leaf. The upper surface color of the young leaf is Yellow-Green Group 144A, suffused with Red Group 46A. The under-surface color of the young leaf is Green Group 139C, suffused with Greyed-Purple Group 183B. The under and upper colors of the leaf veins on the young leaf are similar in coloration to the upper and under surfaces colors of the young leaf.

The mature rachis average is 1.5 cm. in length. The upper side is shallowly grooved. The underside of the mature rachis is moderately rough with very few small prickles. The mature rachis color is Yellow-Green Group 145A, often suffused on the young leaves with Red Group 46A.

The stipules average 1.4 cm. in length and average 0.5 cm. in width, with short straight points that usually turn out at an angle of 45 degrees. The under and upper surface color of the stipule is Yellow-Green Group 145A, often suffused on the young leaves with Red Group 46A. The upper and under surfaces of the stipules are smooth in texture.

The petiole is approximately 2 mm in diameter and smooth. The upper side is shallowly grooved. The petiole 2 cm. in length. The petiole color is Yellow-Green Group 145A, often suffused on the young leaves with Red Group 46A.

The plant displays a high degree of resistance to powdery mildew (*Sphaerotheca pannosa*), and an above average resistance to downy mildew (*Peronospora sparsa*), black spot (*Diplocarpon rosae*) and rust (*Phragmidium* sp.) as compared to other commercial varieties grown under comparable conditions in Tyler, Tex. The plant's winter hardiness has yet to be determined, and the plant's drought/heat tolerance is above average.

Flower

The new cultivar usually bears its flowers in clusters of nine to eleven per stem. Flowers are often borne in grouped clusters that average 17 to 20 cm. in length. The cluster ranges an average from 17 to 20 cm. in diameter. Outdoors, the plant blooms abundantly and nearly continuously during the growing season. The flowers have a slight spice and sweet fragrance.

Bud

The peduncle averages 3.2 to 3.5 cm. in length, of slight caliper (about 0.2 to about 0.3 cm. in diameter), and usually erect. It is slightly rough, with some stipitate glands and few hairs. Peduncle color is Yellow-Green Group 144C and sometimes slightly suffused, especially on the side exposed to the sun, with Greyed-Purple Group 185D.

Before the calyx breaks, the bud averages 1.2 cm. in diameter at the widest point, 1.5 cm. in length, and pointed to somewhat ovoid in shape. The surface of the bud bears between 9 to 11 foliaceous appendages, usually with slender entire foliaceous parts extending beyond the tip of the bud about ¼ or more of its length. Bud color is Yellow-Green Group N144C sometimes slightly suffused, especially on the side exposed to the sun, with Greyed-Purple Group 185D.

The sepals are 5 per flower, average 2.4 cm. in length and about 0.8 cm. in width at the widest point. The outer surface color of the sepal is Yellow-Green Group N144C sometimes slightly suffused, especially on the side exposed to the sun, with Greyed-Purple Group 185D. The outer surface of the sepal is smooth and bears between 0 to 3 foliaceous appendages. The sepals are moderately permanent, and usually straight in shape with attentuate apices.

The receptacle of the flower is short length (0.4 cm. average) and average in caliper (about 0.6 to about 0.8 cm.

in diameter). The receptacle is urn-shaped in form. Its surface is smooth with moderately thick fleshy walls. The receptacle color is Yellow-Green Group N144B.

Bloom

When fully open, the blooms average 9 cm. in diameter. Petalage is double with about 20 to 25 petals and about 1 to 5 petaloids irregularly arranged. When partially open, the bloom form is loosely high centered, and the obovate petals are slightly cupped and slightly reflexed outward. When fully open, the bloom form is slightly flat, and the petals are loosely cupped.

Petals

The petals are of moderately heavy substance and of medium thickness, with inside surfaces slightly velvety and outside slightly satiny. The outer petals are very broadly obovate in shape with a mostly rounded apex, and they are about 3.9 cm long by 3.7 cm wide. The inner petals are somewhat obovate to nearly round in shape with the apex usually rounded to flat, and they are about 3.4 cm long by 3.2 cm wide. The outer petals are somewhat obovate to nearly round in shape with rounded apices. The inner petals are moderately obovate in shape with rounded apices. Petaloids average 0.75 cm in length and about 0.5 cm in width at the widest point. Petaloids are irregularly shaped to somewhat obovate with rounded apices.

Male Reproductive Organs

Stamens are many in number (average about 80) and are arranged regularly about the pistils; a few are mixed with petaloids. The filaments average 0.7 cm. in length. Filaments are Yellow-Orange Group 17A in color. The anthers are of small size for the class and all open approximately at the same time. Anther color is Yellow-Orange Group 17A. Pollen is ample and Yellow-Orange Group 18B in color.

Female Reproductive Organs

Pistils average 100 in number. The styles are moderately even, short in length (about 0.5 cm.), thin in caliper, and loosely bunched. Stigma color is Yellow Group 13B. Style color is Yellow-Green Group 145D. The ovary is enclosed in the receptacle, and the receptacle is approximately 9 mm. in diameter. The ovules within the ovary are less than 1 mm. in diameter and Yellow-White Group 158B in color. Hips and matures seed have not been observed on this cultivar when grown in Tyler, Tex.

Newly Opened Flower

The under-surface color of the outer petals is Orange-Red Group 35A. The upper surface color of the outer petals is Red Group 39A. At the point where the petal attaches, there is a small zone of Yellow Group 13B. The under and upper surface colors of the petaloids are similar in coloration to the upper and under surfaces of the intermediate and inner petals.

The general tonality of the newly opened flower is Red Group 39A.

Three-Day-Old Flower

The under-surface color of the outer petals is Red Group 48A. The upper surface color of the outer petals is Red Group 54A. At the point where the petal attaches, there is a small zone of Yellow-Orange Group 16C. The under and upper surface colors of the petaloids are similar in coloration to the upper and under surfaces of the intermediate and inner petals.

The general tonality of the newly opened flower is Red Group 54A.

On the spent bloom, the petals usually drop off cleanly.

In August in Tyler, Tex. blooms on the bush growing outdoors generally last about four to five days.

The new 'RIPfirst' cultivar has not been observed under all possible environmental conditions to date. Accordingly, it is possible that the phenotypic expression may vary somewhat with changes in light intensity and duration, cultural practices, and other environmental conditions.

The invention claimed is:

1. A new and distinct shrub rose plant named 'RIPfirst' as described and illustrated herein.

* * * * *